(12) United States Patent
Chon et al.

(10) Patent No.: US 12,427,058 B2
(45) Date of Patent: Sep. 30, 2025

(54) BI-MODAL ULTRASONIC HANDPIECE SYSTEM

(71) Applicant: Alcon Inc., Fribourg (CH)

(72) Inventors: James Y. Chon, Irvine, CA (US); Ahmad Salehi, Irvine, CA (US); Kurt D. Leukanech, Laguna Niguel, CA (US); Satish Yalamanchili, Irvine, CA (US); Dan Teodorescu, Irvine, CA (US); Ho Man Michael Fong, Irvine, CA (US)

(73) Assignee: Alcon, Inc., Fribourg (CH)

( * ) Notice: Subject to any disclaimer, the term of this patent is extended or adjusted under 35 U.S.C. 154(b) by 232 days.

(21) Appl. No.: 18/173,864

(22) Filed: Feb. 24, 2023

(65) Prior Publication Data

US 2023/0270591 A1   Aug. 31, 2023

Related U.S. Application Data

(60) Provisional application No. 63/268,624, filed on Feb. 28, 2022.

(51) Int. Cl.
*A61F 9/007* (2006.01)
*A61B 17/00* (2006.01)

(52) U.S. Cl.
CPC ...... *A61F 9/00745* (2013.01); *A61B 2017/00137* (2013.01); *A61B 2017/00402* (2013.01); *A61B 2217/005* (2013.01)

(58) Field of Classification Search
CPC ....... A61F 9/00745; A61B 2017/00137; A61B 2017/00402; A61B 2217/005
See application file for complete search history.

(56) References Cited

U.S. PATENT DOCUMENTS

| | | |
|---|---|---|
| 5,112,300 A | 5/1992 | Ureche |
| 5,279,547 A | 1/1994 | Costin |
| 5,431,664 A | 7/1995 | Ureche |
| 5,808,396 A | 9/1998 | Boukhny |
| 5,938,677 A | 8/1999 | Boukhny |
| 6,028,387 A | 2/2000 | Boukhny |
| 6,077,285 A | 6/2000 | Boukhny |
| 6,402,769 B1 | 6/2002 | Boukhny |
| 6,517,560 B1 | 2/2003 | Toth |
| 6,602,193 B2 | 8/2003 | Chon |
| 6,984,220 B2 | 1/2006 | Wuchinich |
| 6,997,935 B2 | 2/2006 | Anderson et al. |
| 7,229,455 B2 | 6/2007 | Sakurai |
| 7,546,781 B2 | 6/2009 | Takahashi |
| 7,572,242 B2 | 8/2009 | Boukhny |

(Continued)

FOREIGN PATENT DOCUMENTS

WO   2021234619 A1   11/2021

*Primary Examiner* — Andrew P. Restaino (57) ABSTRACT

An ultrasonic handpiece includes a piezoelectric element assembly. Control signals drive the piezoelectric element assembly simultaneously in a first mode of oscillation and a second mode of oscillation. Feedback of a resulting oscillation of the piezoelectric element assembly in the first mode and the second mode is generated. Based on the feedback, the frequency of each of the first mode and second mode is independently adjusted, as needed, so that the resulting oscillation of each of the first mode and the second mode is each approximately at its respective resonant frequency.

12 Claims, 8 Drawing Sheets

(56) References Cited

U.S. PATENT DOCUMENTS

| | | |
|---|---|---|
| 7,871,420 B2 | 1/2011 | Anderson et al. |
| 8,172,786 B2 | 5/2012 | Boukhny |
| 8,303,530 B2 | 11/2012 | Injev et al. |
| 8,303,613 B2 | 11/2012 | Crandall |
| 8,395,299 B2 | 3/2013 | Bromfield |
| 8,512,325 B2 | 8/2013 | Mathonnet |
| 8,545,528 B2 | 10/2013 | Rob et al. |
| 8,579,929 B2 | 11/2013 | Mackool |
| 9,018,887 B2 | 4/2015 | Paschke |
| 9,724,118 B2 | 8/2017 | Schulte |
| 10,016,209 B2 | 7/2018 | Downey et al. |
| 10,258,505 B2 | 4/2019 | Ovchinnikov |
| 10,363,166 B2 * | 7/2019 | Raney ................ A61F 9/00745 |
| 10,478,337 B2 | 11/2019 | Raney |
| 10,561,435 B2 | 2/2020 | Downey et al. |
| 10,786,275 B2 | 9/2020 | Downey |
| 2001/0011176 A1 | 8/2001 | Boukhny |
| 2007/0249942 A1 | 10/2007 | Salehi et al. |
| 2008/0172076 A1 | 7/2008 | Chon et al. |
| 2009/0005712 A1 | 1/2009 | Raney |
| 2010/0268388 A1 * | 10/2010 | Boukhny .............. A61M 3/022 |
| | | 700/283 |
| 2011/0092886 A1 | 4/2011 | Raney |
| 2011/0130780 A1 | 6/2011 | Slipszenko |
| 2013/0035707 A1 | 2/2013 | Giordano |
| 2014/0005707 A1 | 1/2014 | Raney |
| 2017/0143369 A1 * | 5/2017 | Downey ........ A61B 17/320068 |
| 2021/0196513 A1 | 7/2021 | Govari et al. |
| 2021/0330493 A1 * | 10/2021 | Steen ................ A61F 9/00745 |
| 2021/0353461 A1 | 11/2021 | Govari et al. |
| 2021/0353462 A1 | 11/2021 | Fritz et al. |
| 2022/0096269 A1 | 3/2022 | Gliner et al. |
| 2022/0323253 A1 | 10/2022 | Shekhani |
| 2023/0039808 A1 | 2/2023 | Govari et al. |
| 2025/0073067 A1 | 3/2025 | Leukanech et al. |

* cited by examiner

BI-MODAL ULTRASONIC HANDPIECE SYSTEM

FIELD

Examples of ultrasonic systems and methods of controlling ultrasonic devices are disclosed herein. In some examples, systems and methods are disclosed for operating ophthalmic phacoemulsification ultrasonic handpieces.

BACKGROUND INFORMATION

A typical ultrasonic surgical device/system suitable for ophthalmic procedures includes an ultrasonically driven handpiece, an attached hollow working tip, an irrigating sleeve and an electronic control console. The handpiece assembly is attached to the control console by an electric cable and flexible tubing. Through the electric cable, the console varies the power level transmitted by the handpiece to the attached working tip, and the flexible tubing is used to supply irrigation fluid to and draw aspiration fluid from the eye through the handpiece assembly.

In some examples of such devices, the operative part of the handpiece is a centrally-located, hollow resonating bar or horn directly attached to a set of piezoelectric crystals that form a piezoelectric element assembly. The crystals supply the required ultrasonic vibration needed to drive both the horn and the attached working tip during phacoemulsification and are controlled by the console. The crystal/horn assembly is suspended within the hollow body or shell of the handpiece. The handpiece body terminates in a reduced diameter portion or nosecone at the body's distal end. The nosecone is externally threaded to accept the irrigation sleeve. Likewise, the horn bore is internally threaded at its distal end to receive the external threads of the working tip. The irrigation sleeve also has an internally threaded bore that is screwed onto the external threads of the nosecone. The working tip is adjusted so that the tip projects only a predetermined amount past the open end of the irrigating sleeve.

When used to perform phacoemulsification, the ends of the working tip and irrigating sleeve are inserted into a small incision of predetermined width in the cornea, sclera, or other location in the eye tissue in order to gain access to the anterior chamber of the eye. The working tip is ultrasonically vibrated along its longitudinal axis within the irrigating sleeve by the crystal-driven ultrasonic horn, thereby emulsifying upon contact the selected tissue in situ. The hollow bore of the working tip communicates with the bore in the horn which in turn communicates with the aspiration line from the handpiece to the console. A reduced pressure or vacuum source in the console draws or aspirates the emulsified tissue from the eye through the open end of the working tip, the bore of the working tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the working tip.

SUMMARY

In some examples herein, a system is disclosed to operate an ultrasonic handpiece tool that includes a piezoelectric element assembly. In some examples, the system applies control signals to drive the piezoelectric element assembly simultaneously in a first mode of oscillation and a second mode of oscillation. In some examples, the system generates feedback of a resulting oscillation of the piezoelectric element assembly in the first mode and the second mode. In some examples, based on the feedback, the system independently adjusts the frequency of each of the first mode and second mode, as needed, so that the resulting oscillation of each of the first mode and the second mode is each approximately at its respective resonant frequency. In some examples, methods are disclosed for operating ultrasonic devices in a first mode of oscillation and a second mode of oscillation. In some examples, based on the feedback, the method comprises independently adjusting the frequency of each of the first mode and second mode, as needed, so that the resulting oscillation of each of the first mode and the second mode is each approximately at its respective resonant frequency.

BRIEF DESCRIPTION OF THE DRAWINGS

Further embodiments, details, advantages, and modifications will become apparent from the following detailed description of example embodiments, which is to be taken in conjunction with the accompanying drawings.

DETAILED DESCRIPTION

In some example embodiments, an ultrasonic system is disclosed for controlling an ultrasonic handpiece so that multiple modes of oscillation, a longitudinal motion and a torsional motion, can be applied simultaneously using a single piezoelectric element assembly. In other examples embodiments, a method is disclosed for controlling an ultrasonic handpiece in multiple modes of oscillation, a longitudinal motion and a torsional motion, simultaneously using a single piezoelectric element assembly.

Reference will now be made in detail to example embodiments of the present disclosure, some of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, and circuits have not been described in detail so as not to unnecessarily obscure aspects of the embodiments. Wherever possible, like reference numbers will be used for like elements.

Figure 1:
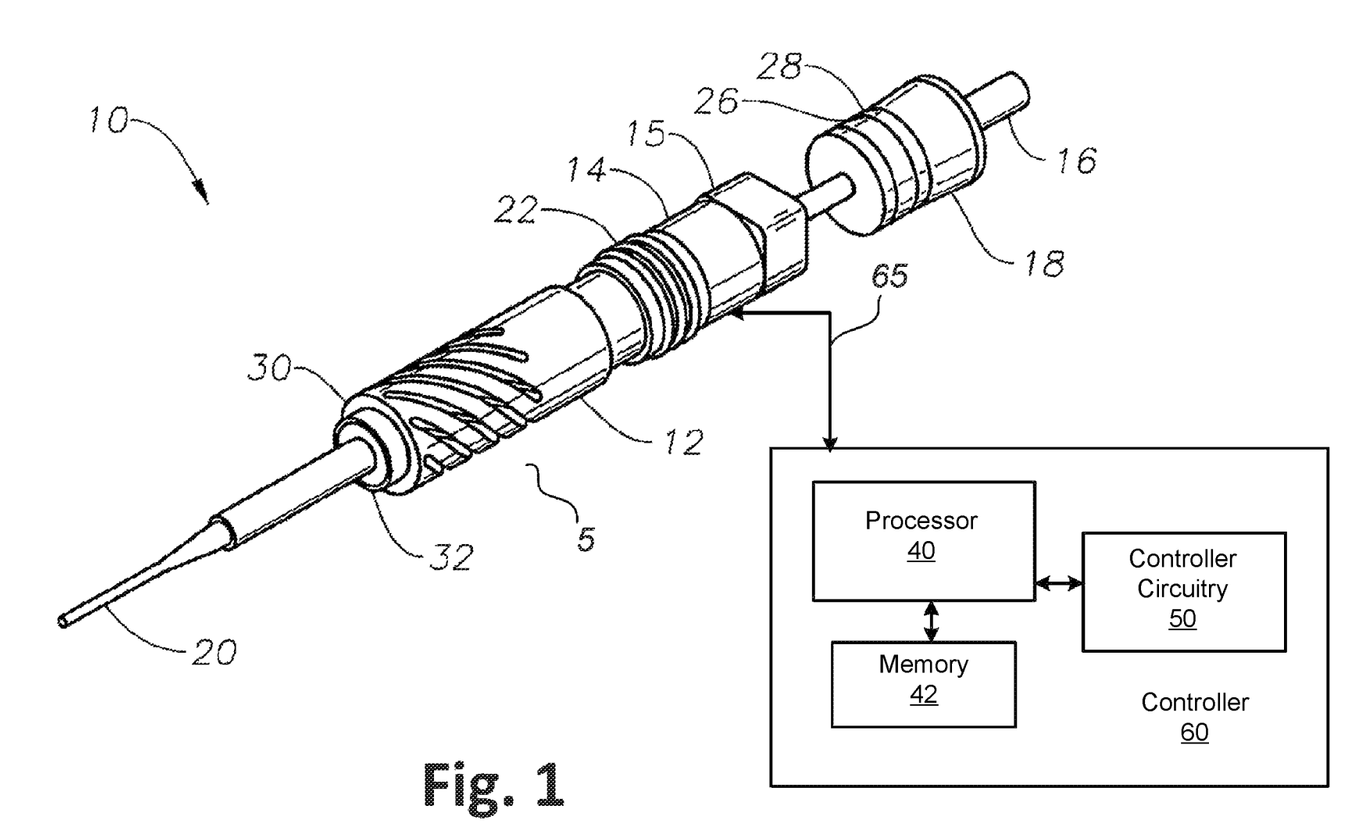
FIG. 1 is a perspective view and block diagram of a bi-modal ultrasonic handpiece system in accordance with some examples.

FIG. 1 is a perspective view and block diagram of a bi-modal ultrasonic handpiece system 10 in accordance with some example embodiments. System 10 may be used, for example, to perform phacoemulsification. FIG. 1 includes a perspective view of the handpiece 5 with the outer case removed, and a block diagram of a controller 60 that controls the handpiece 5. Handpiece 5 includes an ultrasonic horn 12, for example made from a titanium alloy. Horn 12 has a plurality of helical slits. A plurality (typically 1 or 2 pairs or more) of piezoelectric elements or crystals form a piezoelectric element assembly 14. The piezoelectric elements or crystals may be ring-shaped and may be held by a compression nut 15 against horn 12. Some handpieces may include multiple piezoelectric element assemblies 14 that are each physically separated from each other along the longitudinal axis of handpiece 5, and each may form a separate assembly/packaging. Each piezoelectric element assembly 14 may be separately electrically coupled to controller 60.

An aspiration shaft or tube 16 extends down the length of handpiece 5 through horn 12, piezoelectric element assembly 14, nut 15, and plug 18 at the proximal end of handpiece 5. Aspiration tube 16 allows material to be aspirated through a hollow working tip 20, which is attached to horn 12, and through and out handpiece 5. While hollow working tip 20 is shown as a straight tip, other tip configurations may also be used (e.g., a bent tip). Plug 18 seals an outer shell of handpiece 5 fluid tight, allowing handpiece 5 to be autoclaved without adversely affecting piezoelectric element assembly 14. Additional grooves 22 for sealing O-ring gaskets (not shown) may be provided on horn 12.

The location of longitudinal and torsional nodal points (the points with zero velocity of the respective mode) of handpiece 5 are indicated on FIG. 1. The torsional node 26 preferably is located at the proximal longitudinal node 28, so that the torsional node 26 and the longitudinal node 28 are coincident, e.g., both of which are located on plug 18. Handpiece 5 also includes a distal longitudinal node 30 located at reduced diameter portion 32 of horn 12.

Controller 60 is generally located remote from handpiece 5 and can be part of an electronic control console (not shown). Controller 60 is coupled to handpiece 5 at piezoelectric element assembly 14 via an electric cable or connector 65, or may be coupled via other communication means, including wirelessly. The electronic control console is further coupled to handpiece 5 via flexible tubing (not shown) in order to provide irrigation and aspiration.

Controller 60 includes a processor 40, a memory 42, and a controller circuitry 50. Processor 40 may be any type of general purpose processor, or could be a processor specifically designed for handpiece 5, such as an application-specific integrated circuit ("ASIC"). Processor 40 may be the same processor that operates the entire system 10, or may be a separate processor.

Memory 42 can be any type of storage device or non-transitory computer-readable medium, such as random access memory ("RAM") or read-only memory ("ROM"). Memory 42 stores instructions executed by processor 40, including instructions to provide multiple modes (e.g., bi-modal) of oscillation simultaneously (i.e., at the same time) via a single piezoelectric element assembly 14, and other functionality disclosed herein. Controller circuitry 50 also provides functionality, in addition to the functionality of processor 40, for providing multiple modes of oscillation simultaneously via a single piezoelectric element assembly 14. In example embodiments, functionality disclosed herein can be provided by processor 40 and memory 42 (i.e., software based) or by controller circuitry 50 (i.e., hardware based) or a combination of both.

The control of ultrasonic motion for a handpiece such as handpiece 5 can be implemented by a number of different methods. One method involves a control loop which servos the frequency of the drive voltage by using the electrical impedance of the piezoelectric drive transducers as feedback. In such a method, the impedance feedback of the piezo-electric transducers is computed as the ratio of the root mean square ("RMS") value of the transducer drive voltage to the RMS value of drive current.

In certain instances, there are advantages in utilizing two or more different modes of oscillation, such as orthogonal longitudinal modes and torsional modes, in an ultrasonic handpiece. However, each mode of oscillation has a distinct resonance of operation which must be independently controlled to maintain the optimal operational frequency in response to various influences such as loading and temperature.

In some known ultrasonic handpiece systems, the handpieces are controlled to provide an ultrasonic longitudinal motion of the cutting tip and a rotational/torsional motion of the tip. Such known ultrasonic handpiece systems for phacoemulsification may include a drive circuit that monitors both the torsional mode and the longitudinal mode and controls these modes using two different drive frequencies. The torsional drive signal is approximately 31 kHz (kilohertz) and the longitudinal drive signal is approximately 45 kHz, but these frequencies may change depending upon the piezoelectric element assemblies 14 used and the size and shape of horn 12 and slits 24. The frequencies of both the longitudinal and torsional modes are tracked and controlled so that the frequencies of these motions are generally at the respective resonant frequencies when being applied.

However, known systems for providing both a longitudinal motion and a torsional motion generally alternate these motions on a single piezoelectric element assembly 14, or use multiple different piezoelectric element assemblies 14 for each different motion. Known systems fail to determine the resonance frequency of both modes simultaneously and fail to simultaneously make the necessary adjustments in the frequency of operations of both modes in order to maintain optimal resonant frequency for both modes in reaction to the various factors that shift the resonant frequencies, such as temperature.

Figure 2:
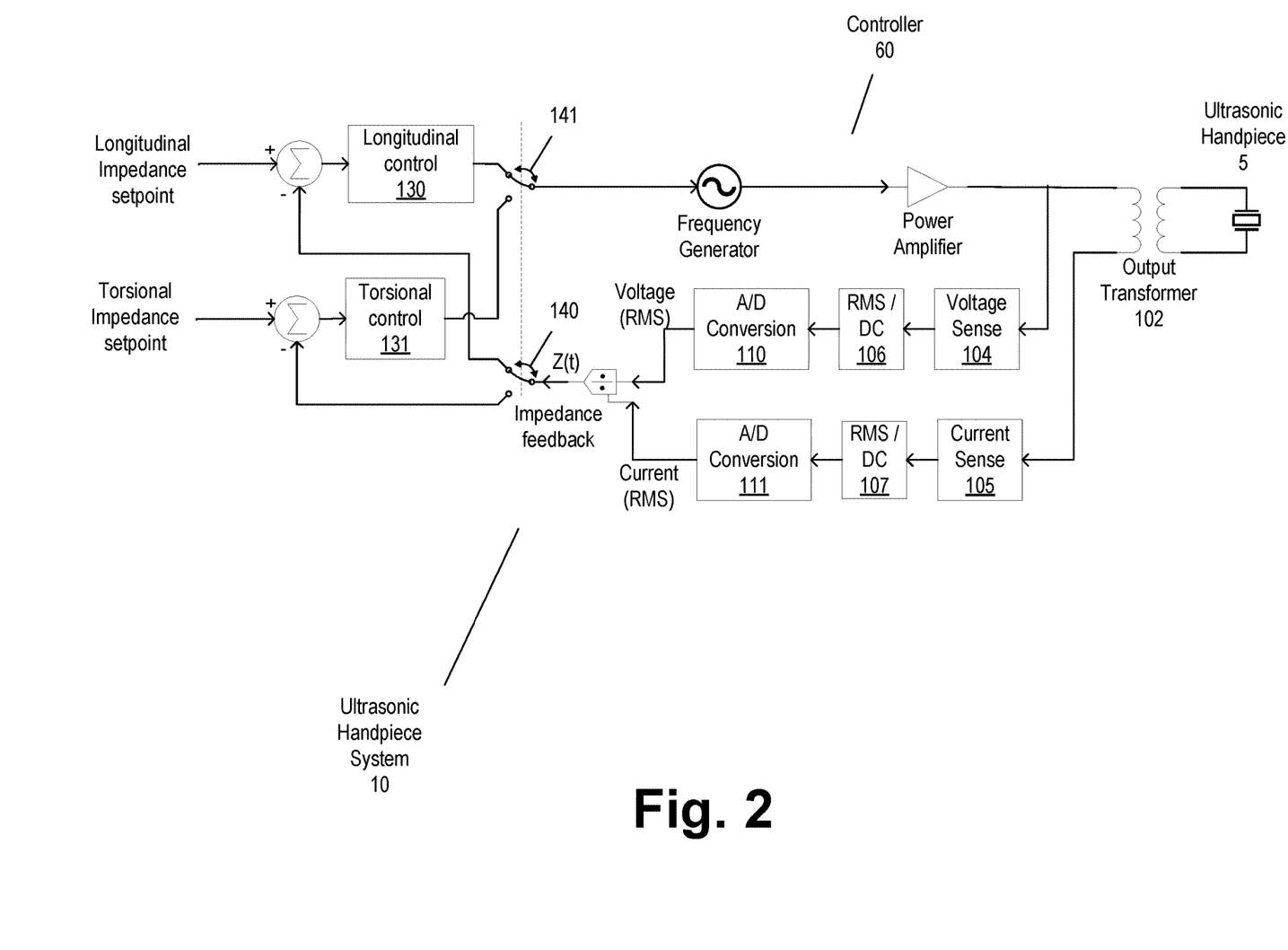
FIG. 2 is a detailed block diagram of the ultrasonic handpiece system of FIG. 1 in accordance with some examples.

FIG. 2 is a detailed block diagram of ultrasonic handpiece system 10 in accordance with some examples. FIG. 2 illustrates details of controller 60 that is coupled to ultrasonic handpiece 5. In general, in FIG. 2, controller 60 tracks resonance by measuring the electrical impedance (i.e., a measurement of voltage and current) reflected back to a primary of an output transformer 102. The RMS value voltage is measured by an RMS to DC converter, RMS/DC 106, and voltage sense 104, and the current (at the same time as the voltage) is measured by RMS/DC 107 and current sense 105, and A/D (analog-to-digital) converters 110 and 111. The measurements generate an impedance feedback 120 ("Z(t)"). Based on the measured impedance feedback, control loops 130 and 131 adjust the frequency to maintain resonance frequency. The longitudinal control 130 and torsional control 131 provide the adjustments separately using switching functionality 140 and 141 where the switching is always in either a longitudinal control position as shown in FIG. 2, or the opposite positions for a torsional control position.

With the embodiment of FIG. 2, when operating multiple modes of oscillation, the RMS value of measured voltage and resulting current is an indication of the aggregate of all component frequencies present in the voltage and current signals being measured. As a result, with embodiments of FIG. 2, it is not possible to independently separate the information (i.e., impedance magnitude) for each resonance to be controlled.

Figure 3A:
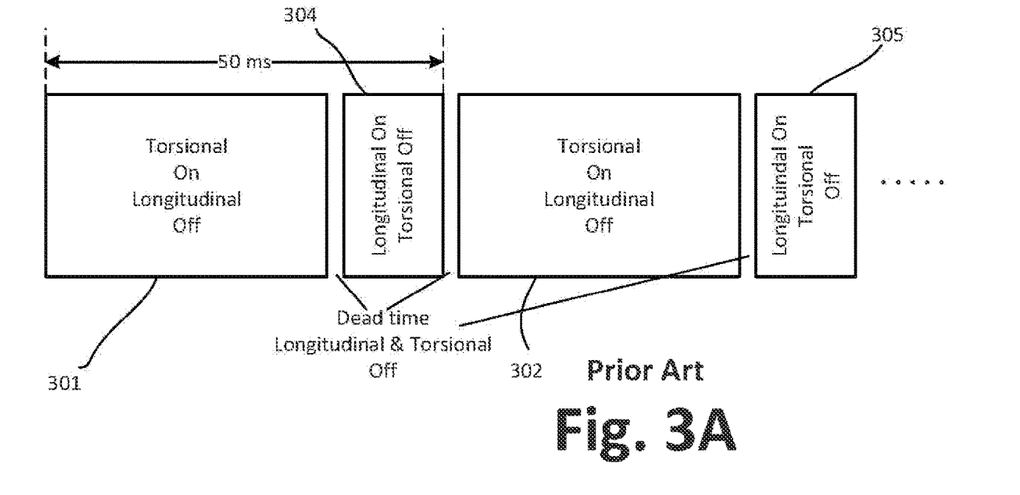
FIG. 3A illustrates a prior art timing diagram for operating an ultrasonic handpiece using a controller.

FIG. 3A illustrates a prior art timing diagram for operating an ultrasonic handpiece using a controller similar to controller 60 of FIG. 2, but with different control functionality. In FIG. 3A, torsional mode and longitudinal mode are applied separately to a single piezoelectric element 14. Specifically, at 301 torsional mode is applied and longitudinal mode is off (i.e., when 140 and 141 are switched to the torsional control). At 302, longitudinal mode is applied and torsional mode is off (i.e., when 140 and 141 are switched to the longitudinal control). During "dead" times 304 and 305, neither of the modes are applied and the respective mode that was applied previously is adjusted by either control loop 130 or 131 to maintain the respective resonant frequency based on the impedance feedback. This "dead" time is necessary to allow the energy from one mode to decay prior to exciting the alternate mode. However, as shown in FIG. 3A, because the alternate modes of oscillation are multiplexed in time as opposed to being applied simultaneously, tissue cutting efficiency is sacrificed when used, for example, to perform phacoemulsification.

Figure 3B:
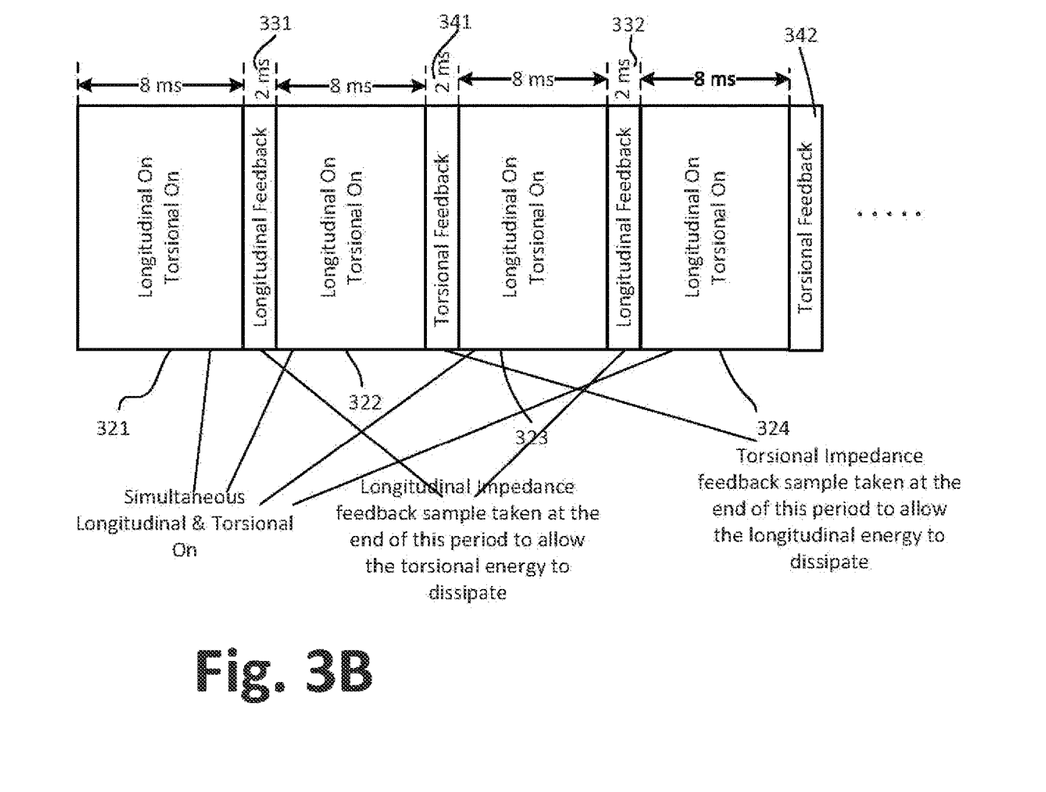
FIG. 3B illustrates a timing diagram for operating an ultrasonic handpiece using the controller of FIG. 2 in accordance with some examples.

FIG. 3B illustrates a timing diagram for operating ultrasonic handpiece 5 using controller 60 of FIG. 2 in accordance with some example embodiments. In contrast to FIG. 3A, during periods 321-324, both longitudinal mode and torsional mode are applied simultaneously to a single piezoelectric element 14 (i.e., exciting the piezoelectric element with both longitudinal and torsional frequencies at the same time) while maintaining independent control of each mode of oscillation. During feedback periods 331 and 332, a longitudinal impedance feedback sample is taken while the longitudinal mode is turned on and the torsional mode is off to allow the torsional energy to dissipate. Similarly, during feedback periods 341 and 342, a torsional impedance feedback sample is taken while the torsional mode is turned on and the longitudinal mode is off to allow the longitudinal energy to dissipate.

FIG. 3B provides for the timing of the feedback such that the simultaneous application of multiple modes of oscillation can be maintained with a high duty cycle. In the timing shown in FIG. 3B, the simultaneous application of multiple modes of oscillation on a single piezoelectric element 14 is active approximately 80% of the time. In this operational mode there is an alternation in time between longer periods of the simultaneous drive periods 321-324 followed by brief periods of feedback measurement periods 331, 332, 341, 342. Each feedback period is used to sample the feedback of one mode of oscillation, and alternating feedback periods alternate between the modes for feedback. In one example, each simultaneous drive period 321-324 may last 8 ms (milliseconds), followed by a feedback measurement period 331, 341, 332, 342 of 2 ms.

Figure 4:
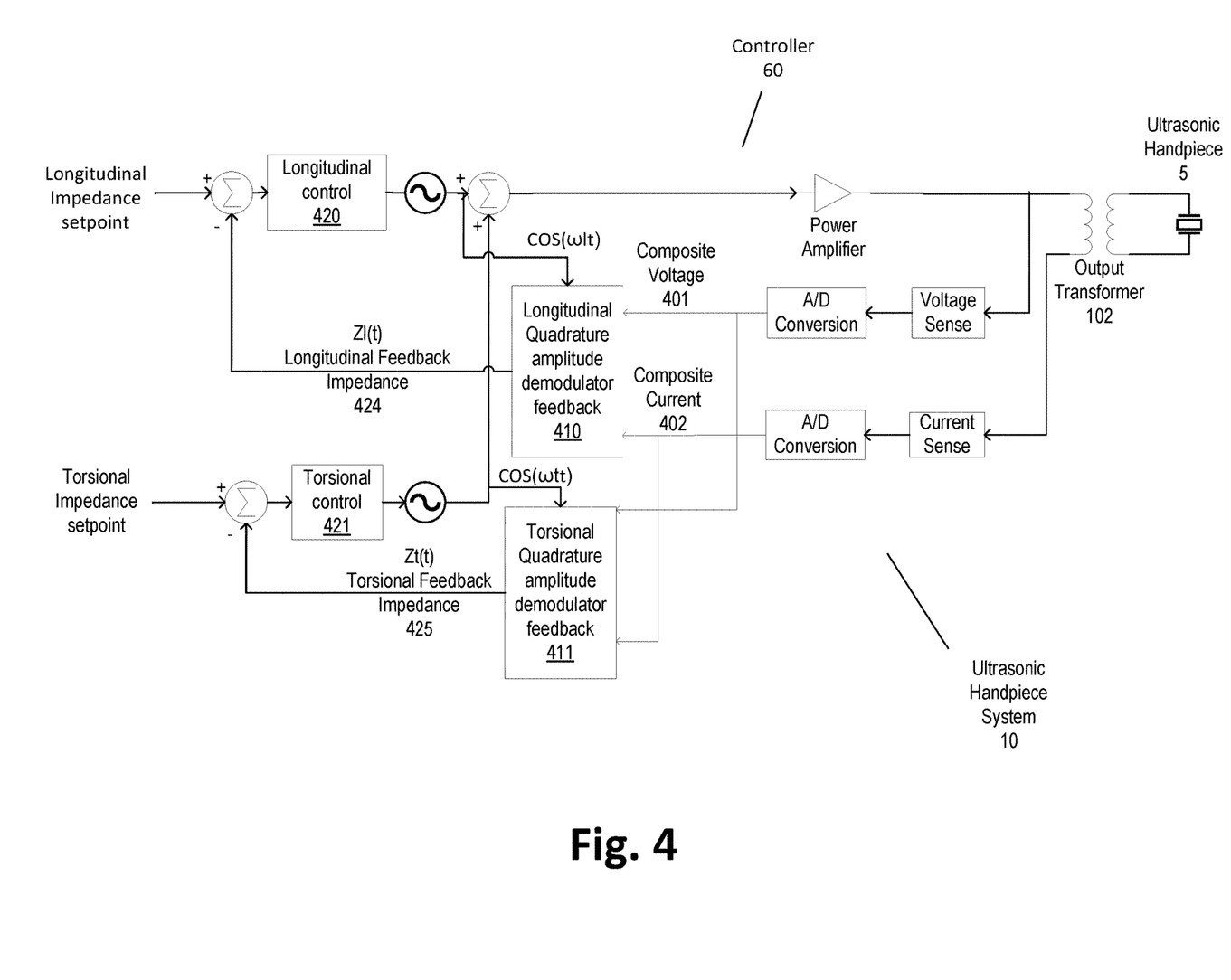
FIG. 4 is a detailed block diagram of a bi-modal ultrasonic handpiece system in accordance with additional examples.

FIG. 4 is a detailed block diagram of ultrasonic handpiece system 10 in accordance with additional example embodiments. In contrast to the embodiments of FIGS. 2 and 3B, where the simultaneous application of multiple modes of oscillation on a single piezoelectric element 14 is active less than 100% of the time, e.g., approximately 80% of the time, in FIG. 4 the simultaneous application is active 100% of the time. Further in contrast to the embodiments of FIGS. 2 and 3B, which samples the RMS value, in FIG. 4 the composite voltage 401 and current 402 are sampled such that the magnitude and phase of each of the independent modes of oscillation may be extracted. FIG. 4 includes a longitudinal quadrature amplifier demodulator 410 and a torsional quadrature amplifier demodulator 411 that extract the specific oscillation mode feedback. The extracted longitudinal impedance magnitude 424 ("Zl(t)") and torsional impedance magnitude 425 ("Zt(t)") is then fed back to control loops 420 and 421, respectively. The functionality of FIG. 4 continuously applies the multiple drive modes as well as feedback for each oscillation mode in a continuous and simultaneous manner as follows, where "mode1" is the longitudinal mode (in FIG. 4, "$\omega l$" is the longitudinal angular frequency (Radians/second) and "$\omega l t$" is the longitudinal angular frequency multiplied by time (seconds)) and "mode2" is the torsional mode (in FIG. 4, "$\omega t$" is the torsional frequency (Radians/second) and "$\omega t t$" is the torsional angular frequency multiplied by time (seconds)"):

$$V_{out} = (V_{mode1} * \cos(\omega_{mode1} * t + \varnothing_{mode1}) + V_{mode2} * \cos(\omega_{mode2} * t + \varnothing_{mode2})) \quad (1)$$

Figure 5:
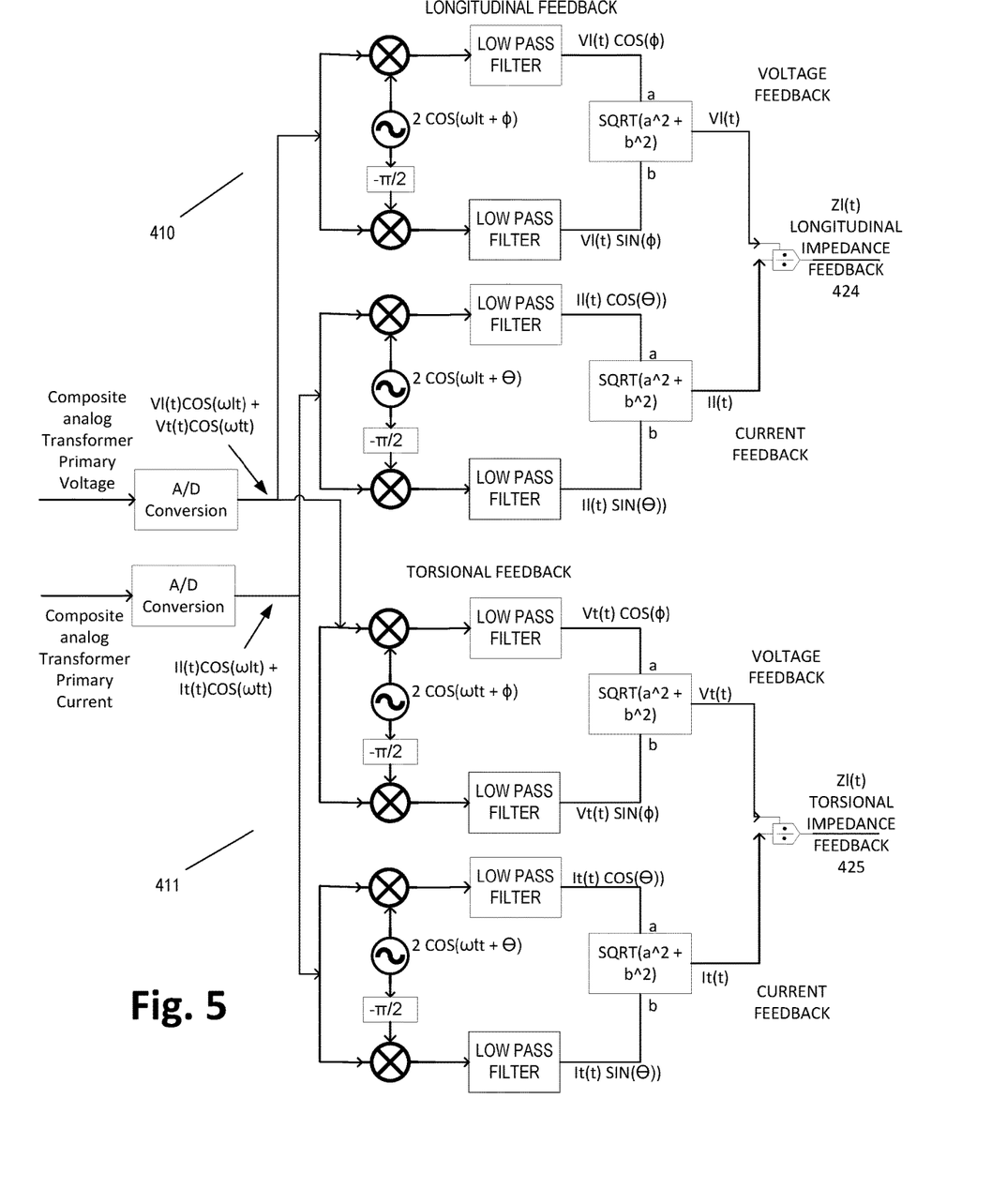
FIG. 5 is a detailed block diagram of the longitudinal quadrature amplitude demodulator and torsional quadrature amplitude demodulator of FIG. 4 in accordance with some examples.

FIG. 5 is a detailed block diagram of a longitudinal quadrature amplitude demodulator 410 and torsional quadrature amplitude demodulator 411 that may be used in the example of FIG. 4 in accordance with some example embodiments. As shown in FIG. 5, demodulators 410 and 411 implement equation (1) above and provide a mixing function that isolates the sinusoidal signal produced by the longitudinal and torsional forces generated simultaneously on a single piezoelectric element 14. In contrast, the embodiment of FIG. 2 does not digitize the entire sinusoidal signal as it only digitizes the envelope of the RMS value. FIG. 5 digitizes the composite signal which is used to extract the amplitude/magnitude information of each mode of oscillation. In FIG. 5, "V" refers to voltage, "I" refers to current, "$\theta$" refers to the current phase angle, and "$\phi$" refers to the voltage phase angle.

Figure 6:
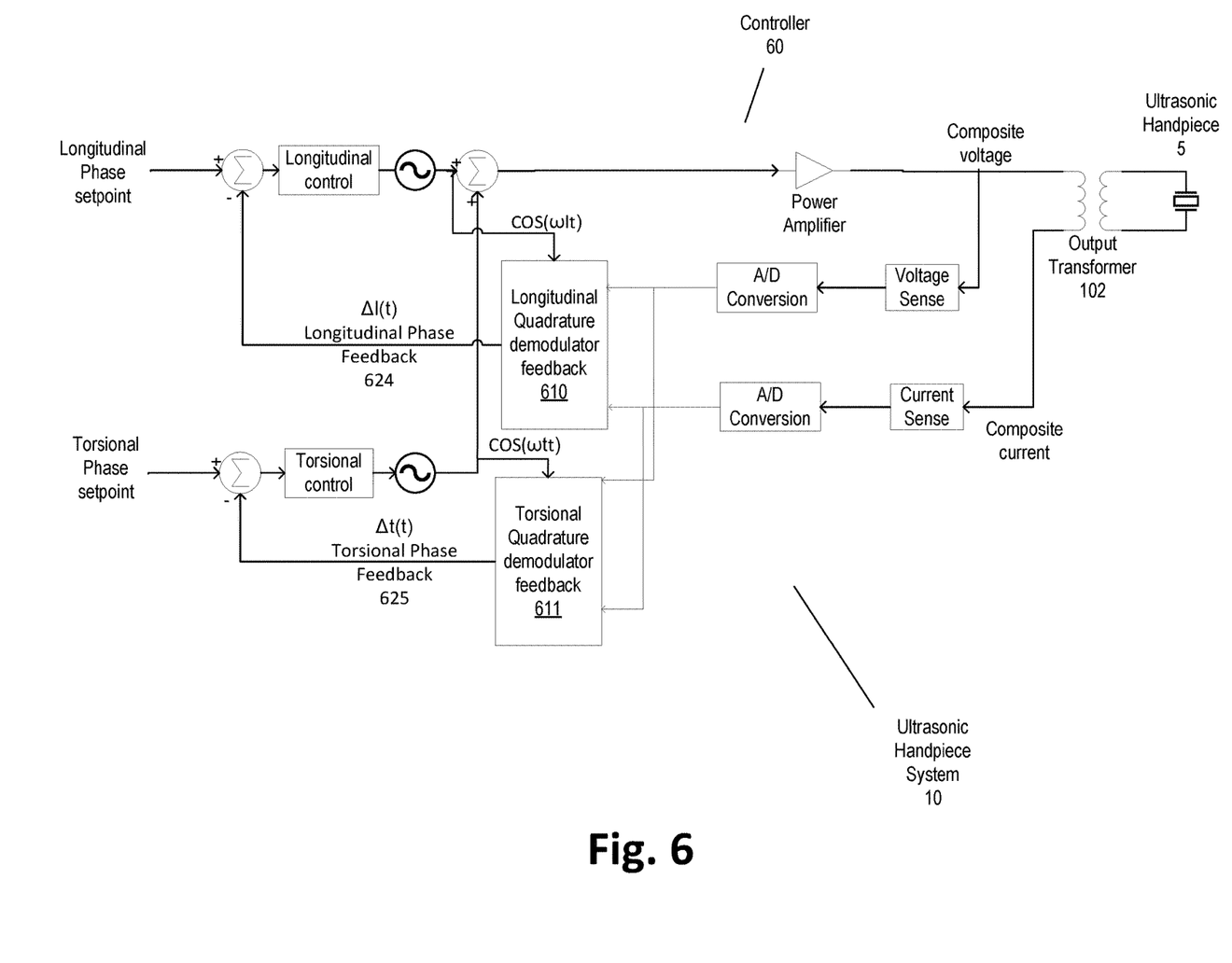
FIG. 6 is a detailed block diagram of a bi-modal ultrasonic handpiece system in accordance with additional examples.

FIG. 6 is a detailed block diagram of ultrasonic handpiece system 10 in accordance with additional example embodiments. The embodiment of FIG. 6 is similar to the embodiment of FIG. 4. However, instead of the magnitude of the impedance being used for feedback, the phase of the impedance is used. A longitudinal quadrature phase demodulator 610 generates a longitudinal phase feedback 624 ("$\Delta l(t)$") and torsional quadrature phase demodulator 611 generates a torsional phase feedback 625 ("$\Delta t(t)$").

Figure 7:
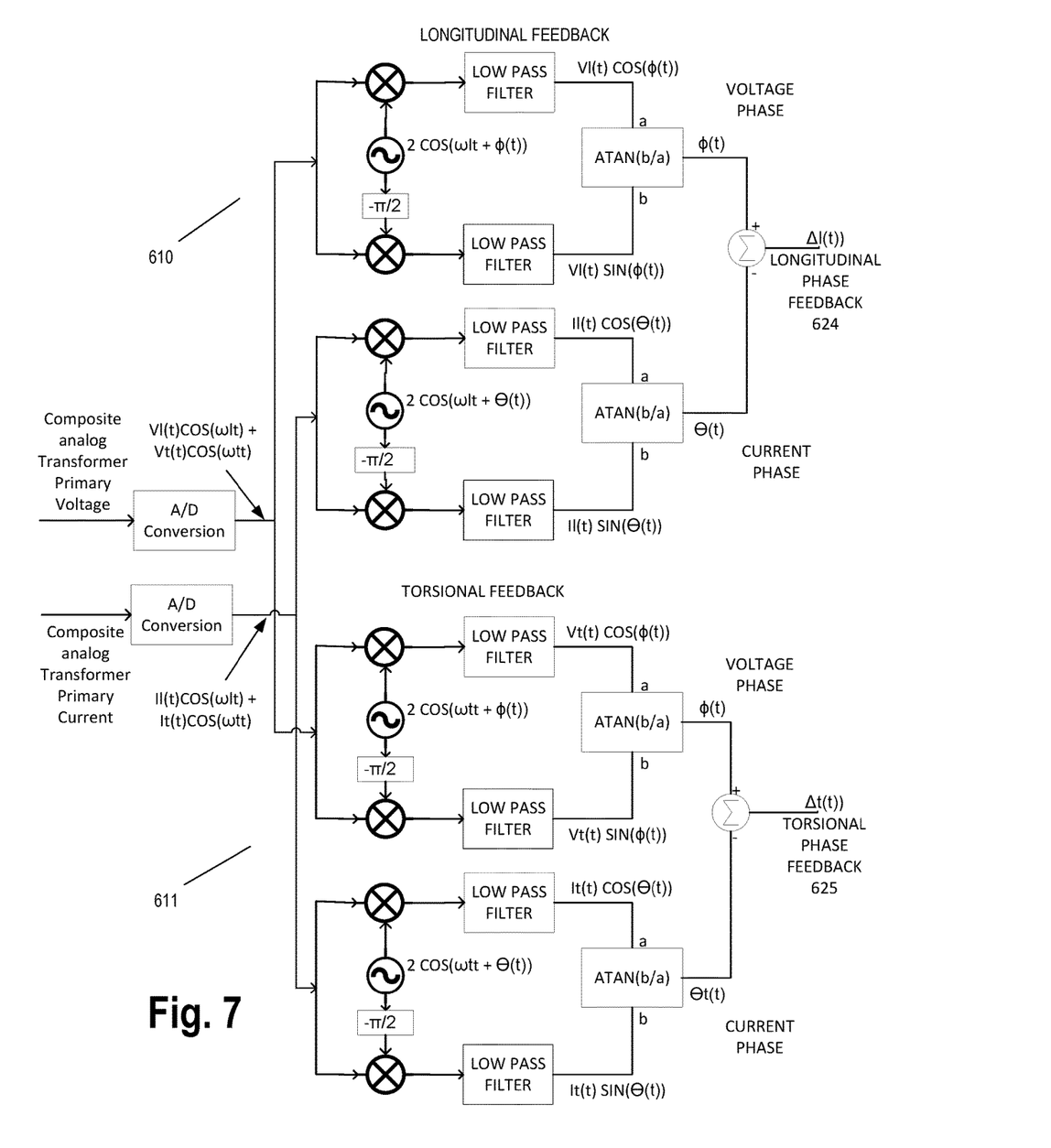
FIG. 7 is a detailed block diagram of the longitudinal quadrature phase demodulator and torsional quadrature phase demodulator of FIG. 6 in accordance with some examples.

FIG. 7 is a detailed block diagram of a longitudinal quadrature phase demodulator 610 and torsional quadrature phase demodulator 611 that may be used in the example of FIG. 6 in accordance with some example embodiments. FIG. 7 is used to extract the phase information.

In other embodiments, a controller combines aspects of controller 60 of FIG. 4 and controller 60 of FIG. 6 to improve the stability of the feedback control, minimizing losses and having improved efficiency. In one embodiment, control of both amplitude/magnitude and phase are combined.

In another embodiment, both the primary and secondary side of the transformer resonant frequency are combined (in contrast to the embodiments of FIGS. 2, 4 and 6 where only the primary side resonant frequency is monitored). Instead of feedback control to find the primary resonant frequency, embodiments include two feedback loops such that the phase is adjusted appropriately based on achieving the best secondary side frequency and the outside loop would be to drive the amplitude to achieve the primary resonant frequency.

In another embodiment, non-linear feedback control of frequency is implemented where the controller gain and integral time are automatically adjusted according to the control error.

Figure 8:
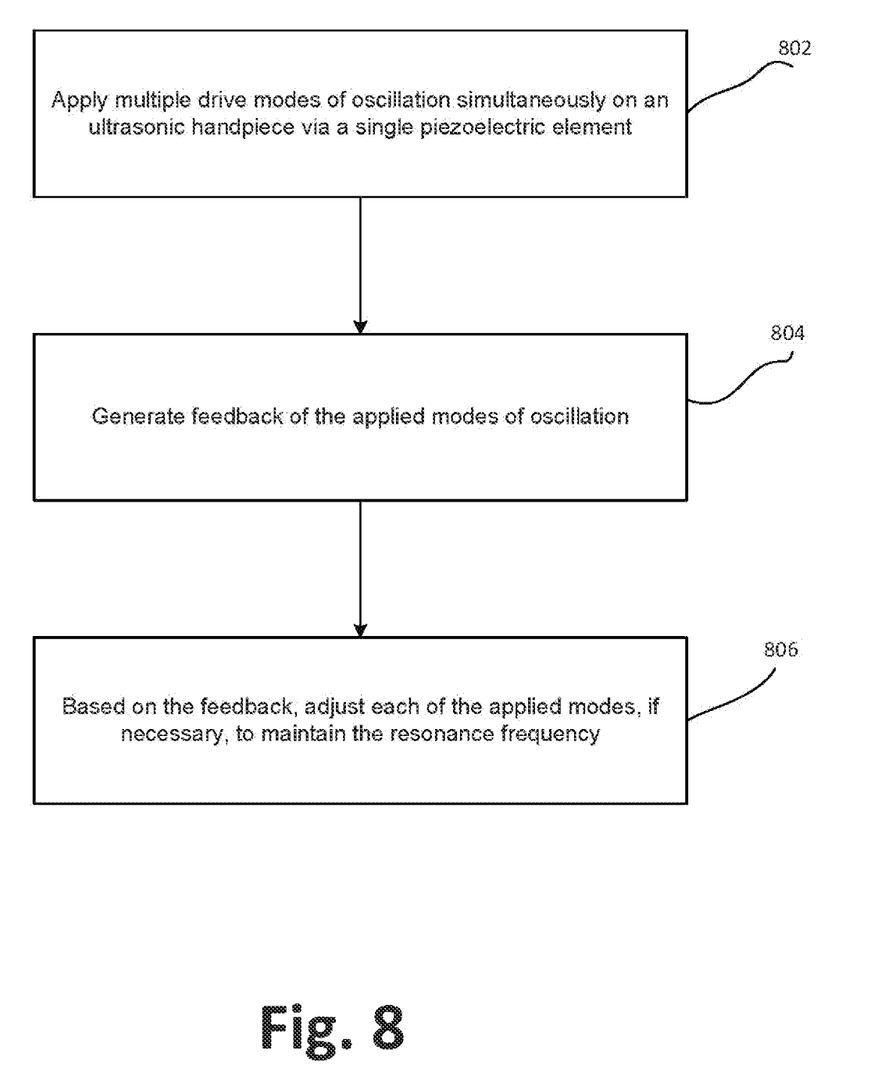
FIG. 8 is a flow diagram of an example of functionality of the controller of FIG. 1 for providing multiple modes of oscillation simultaneously for an ultrasonic handpiece via a single piezoelectric element assembly in accordance with some examples disclosed herein.

FIG. 8 is a flow diagram of an example of the functionality of controller 60 of FIG. 1 for providing multiple modes of oscillation simultaneously for an ultrasonic handpiece 5 via a single piezoelectric element 14 in accordance with one embodiment. In one embodiment, the functionality of the flow diagram of FIG. 8 is implemented by software stored in memory or other computer readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software.

At 802, multiple drive modes of oscillation are applied simultaneously on an ultrasonic handpiece via a single piezoelectric element. In embodiments, the multiple modes of oscillation are a torsional drive signal, e.g., of approximately 31 kHz, and a longitudinal drive signal, e.g., of approximately 45 kHz. Other frequencies can be used in other embodiments. Each mode has a resonance frequency of operation that should be maintained in order to optimize efficiency and effectiveness.

At 804, feedback of the applied modes of oscillation is generated. In one embodiment, the feedback is based on RMS values of each of the modes. In other embodiments, the feedback is based on the magnitude of the combined modes. In another embodiment, the feedback is based on the phase of the combined modes. In some embodiments, the feedback is generated in an interim period when only one of the modes is being applied. In other embodiments, the feedback is generated at the same time that both modes are being applied.

At 806, based on the feedback, each of the applied modes is adjusted, if necessary, to maintain the resonance frequency. The adjustment may include independently adjusting the frequency of the constituent components of the drive voltage so that the resulting oscillation of each mode is approximately at its resonant frequency.

Experimental results for phacoemulsification compared known systems (e.g., FIG. 3A), in which a longitudinal mode and torsional mode are applied on a single piezoelectric element separately ("separate"), to embodiments of the invention in which a longitudinal mode and torsional mode are applied on a single piezoelectric element simultaneously ("simultaneous"). In the results, the average phaco time was 5.48 seconds per milligram ("s/mg") for separate compared to 2.79 s/mg for simultaneous. The average efficiency was 6.79 joules per milligram ("j/mg") for separate compared to 1.09 j/mg for simultaneous. The total efficiency improvement of simultaneous compared to separate is a 49.13% time reduction.

As disclosed, embodiments operate an ultrasonic handpiece, such as a phacoemulsifier, by applying multiple modes of oscillation simultaneously using a single set of piezoelectric elements that form a piezoelectric element assembly.

The features, structures, or characteristics of the disclosure described throughout this specification may be combined in any suitable manner in one or more embodiments. For example, the usage of "one embodiment," "some embodiments," "certain embodiment," "certain embodiments," or other similar language, throughout this specification refers to the fact that a particular feature, structure, or characteristic described in connection with the embodiment may be included in at least one embodiment of the present disclosure. Thus, appearances of the phrases "one embodiment," "some embodiments," "a certain embodiment," "certain embodiments," or other similar language, throughout this specification do not necessarily all refer to the same group of embodiments, and the described features, structures, or characteristics may be combined in any suitable manner in one or more embodiments.

One having ordinary skill in the art will readily understand that the embodiments as discussed above may be practiced with steps in a different order, and/or with elements in configurations that are different than those which are disclosed. Therefore, although this disclosure considers the outlined embodiments, it would be apparent to those of skill in the art that certain modifications, variations, and alternative constructions would be apparent, while remaining within the spirit and scope of this disclosure. In order to determine the metes and bounds of the disclosure, therefore, reference should be made to the appended claims.

What is claimed is:

1. A method of operating an ultrasonic handpiece comprising a piezoelectric element assembly, the method comprising:
   applying control signals to drive the piezoelectric element assembly simultaneously in a first mode of oscillation and a second mode of oscillation;
   generating feedback of a resulting oscillation of the piezoelectric element assembly for each of the first mode and the second mode; and
   based on the feedback, adjusting the applied control signals so that the resulting oscillation in the first mode and the resulting oscillation in the second mode are each approximately at a respective resonant frequency;
   wherein the generating feedback comprises determining a magnitude of a composite voltage and a composite current of the resulting oscillation in the first and second modes.

2. The method of claim 1, wherein the first mode of oscillation comprises a longitudinal motion and the second mode of oscillation comprises a torsional motion.

3. The method of claim 1, wherein the ultrasonic handpiece comprises a phacoemulsifier.

4. The method of claim 1, wherein the piezoelectric element assembly comprises one or more pairs of ring-shaped piezoelectric elements.

5. The method of claim 1, wherein the ultrasonic handpiece comprises an additional piezoelectric element assembly, and wherein each piezoelectric element assembly is spaced apart along a longitudinal axis of the ultrasonic handpiece.

6. The method of claim 1, wherein the ultrasonic handpiece comprises an ultrasonic horn, an aspiration tube, and a hollow tip.

7. A method of operating an ultrasonic handpiece comprising a piezoelectric element assembly, the method comprising:
   applying control signals to drive the piezoelectric element assembly simultaneously in a first mode of oscillation and a second mode of oscillation;

generating feedback of a resulting oscillation of the piezoelectric element assembly for each of the first mode and the second mode; and based on the feedback, adjusting the applied control signals so that the resulting oscillation in the first mode and the resulting oscillation in the second mode are each approximately at a respective resonant frequency;

wherein the generating feedback comprises determining a phase of a composite voltage and a composite current of the resulting oscillation in the first and second modes.

8. The method of claim 7, wherein the first mode of oscillation comprises a longitudinal motion and the second mode of oscillation comprises a torsional motion.

9. The method of claim 7, wherein the ultrasonic handpiece comprises a phacoemulsifier.

10. The method of claim 7, wherein the piezoelectric element assembly comprises one or more pairs of ring-shaped piezoelectric elements.

11. The method of claim 7, wherein the ultrasonic handpiece comprises an additional piezoelectric element assembly, and wherein each piezoelectric element assembly is spaced apart along a longitudinal axis of the ultrasonic handpiece.

12. The method of claim 7, wherein the ultrasonic handpiece comprises an ultrasonic horn, an aspiration tube, and a hollow tip.

* * * * *